US012685835B2

(12) United States Patent　　　　　(10) Patent No.:　US 12,685,835 B2
　　　Liew et al.　　　　　　　　　　　　(45) Date of Patent:　　　Jul. 21, 2026

(54) FUNNELED T-CONNECTOR WITH NEBULIZER FOR USE WITH A POSITIVE PRESSURE VENTILATOR

(71) Applicant: HILL-ROM SERVICES PTE. LTD., Singapore (SG)

(72) Inventors: Justin Xuan Kai Liew, Singapore (SG); Baoyi Wu, Singapore (SG); Deny Duay Barilea, Singapore (SG); Song Chiun Yong, Johor (MY)

(73) Assignee: HILL-ROM SERVICES PTE. LTD., Singapore (SG)

( * ) Notice: Subject to any disclaimer, the term of this patent is extended or adjusted under 35 U.S.C. 154(b) by 898 days.

(21) Appl. No.: 17/706,693

(22) Filed: Mar. 29, 2022

(65)　　　　　　Prior Publication Data

US 2022/0347420 A1　　　Nov. 3, 2022

Related U.S. Application Data

(60) Provisional application No. 63/183,239, filed on May 3, 2021.

(51) Int. Cl.
A61M 16/08　　　　(2006.01)
A61M 11/02　　　　(2006.01)
　　　　　(Continued)

(52) U.S. Cl.
CPC ........ A61M 16/0833 (2014.02); A61M 11/02 (2013.01); A61M 16/0054 (2013.01);
　　　　　(Continued)

(58) Field of Classification Search
CPC .............. A61M 11/02; A61M 15/0086; A61M 16/0833; A61M 16/0054; A61M 16/0402;
　　　　　(Continued)

(56)　　　　　　References Cited

U.S. PATENT DOCUMENTS 3,301,255 A　*　1/1967　Thompson ............ A61M 16/16
　　　　　　　　　　　　　　　　　　128/200.21
4,259,951 A　*　4/1981　Chernack ............ F16K 15/1402
　　　　　　　　　　　　　　　　　　128/205.24
　　　　　　　　(Continued)

FOREIGN PATENT DOCUMENTS

CN　　　203749970 U　　8/2014
CN　　　203763601 U　　8/2014
　　　　　　　　(Continued)

OTHER PUBLICATIONS

Extended European Search Report for European Patent Application No. 22799212.0 dated Feb. 12, 2025 (10 pages).
　　　　　　　　(Continued)

*Primary Examiner* — Tu A Vo
(74) *Attorney, Agent, or Firm* — Barnes & Thornburg LLP

(57)　　　　　　ABSTRACT

An apparatus for applying positive pressure nebulized liquid to a patient includes a funneled T-connector having a funnel with a first opening of a first diameter, a second opening of a second diameter smaller than the first diameter, and a funnel wall extending between the first and second openings. The funneled T-connector further has a cylindrical nebulizer port that extends outwardly from the funnel wall. A nebulizer cup assembly includes a nebulizer cup to contain liquid and a nebulizer cap to removably attach to a top region of the nebulizer cup. The nebulizer cap has a cylindrical nebulizer outlet sized to removably attach to the cylindrical nebulizer port. The cylindrical nebulizer outlet extends upwardly through the nebulizer passage, beyond the cylindrical nebulizer port, and into the internal funnel space such that a top edge of the cylindrical nebulizer outlet is located within the internal funnel space.

30 Claims, 8 Drawing Sheets

(51) Int. Cl.

| | |
|---|---|
| *A61M 11/06* | (2006.01) |
| *A61M 15/00* | (2006.01) |
| *A61M 16/00* | (2006.01) |
| *A61M 16/04* | (2006.01) |
| *A61M 16/06* | (2006.01) |
| *A61M 16/10* | (2006.01) |
| *A61M 16/12* | (2006.01) |
| *A61M 16/14* | (2006.01) |

(52) U.S. Cl.

CPC .... *A61M 16/0402* (2014.02); *A61M 16/0883* (2014.02); *A61M 16/14* (2013.01); *A61M 11/06* (2013.01); *A61M 15/0021* (2014.02); *A61M 16/0063* (2014.02); *A61M 16/0066* (2013.01); *A61M 16/04* (2013.01); *A61M 16/06* (2013.01); *A61M 16/0808* (2013.01); *A61M 16/107* (2014.02); *A61M 16/125* (2014.02)

(58) Field of Classification Search

CPC .. A61M 15/0021; A61M 16/04; A61M 16/06; A61M 16/0883; A61M 16/0808; A61M 16/107; A61M 16/125; A61M 2209/02; A61M 16/0006; A61M 16/14; A61M 11/06; A61M 16/0063; A61M 16/0066

See application file for complete search history.

(56) References Cited

U.S. PATENT DOCUMENTS

| | | | | |
|---|---|---|---|---|
| 4,560,519 A | * | 12/1985 | Cerny | A61M 11/06 261/78.2 |
| 4,657,007 A | * | 4/1987 | Carlin | A61M 11/002 128/200.21 |
| 4,829,998 A | * | 5/1989 | Jackson | A61M 16/16 128/203.12 |
| 4,852,563 A | | 8/1989 | Gross | |
| 4,951,661 A | * | 8/1990 | Sladek | A61M 16/0808 128/205.24 |
| 5,020,530 A | * | 6/1991 | Miller | A61M 16/0833 128/205.13 |
| 5,036,840 A | * | 8/1991 | Wallace | A61M 15/0086 128/203.12 |
| 5,277,175 A | * | 1/1994 | Riggs | A61M 16/0858 128/203.14 |
| 5,435,297 A | * | 7/1995 | Klein | A61M 15/0021 239/296 |
| 5,546,930 A | * | 8/1996 | Wikefeldt | A61M 16/0833 128/207.14 |
| 5,570,682 A | * | 11/1996 | Johnson | A61M 11/06 128/200.14 |
| 5,823,179 A | * | 10/1998 | Grychowski | A61M 15/0021 239/338 |
| 6,328,030 B1 | | 12/2001 | Kidwell et al. | |
| 6,550,476 B1 | | 4/2003 | Ryder | |
| 6,708,688 B1 | | 3/2004 | Rubin et al. | |
| 6,718,969 B1 | | 4/2004 | Rubin et al. | |
| 6,725,858 B2 | | 4/2004 | Loescher | |
| 6,792,946 B1 | | 9/2004 | Waldo et al. | |
| 7,191,780 B2 | | 3/2007 | Faram | |
| 7,201,167 B2 | | 4/2007 | Fink et al. | |
| 7,267,121 B2 | * | 9/2007 | Ivri | A61M 16/0833 128/200.14 |
| 7,721,734 B2 | | 5/2010 | Rustad et al. | |
| 7,909,033 B2 | | 3/2011 | Faram | |
| 8,051,854 B2 | | 11/2011 | Faram | |
| 8,365,727 B2 | | 2/2013 | Dunsmore et al. | |
| 8,485,179 B1 | | 7/2013 | Meyer et al. | |
| 8,539,952 B2 | | 9/2013 | Carbone et al. | |
| 8,573,203 B2 | | 11/2013 | Addington et al. | |
| 8,931,478 B2 | | 1/2015 | Dunsmore et al. | |
| 9,050,434 B2 | | 6/2015 | Faram | |
| 9,151,425 B2 | | 10/2015 | Faram | |
| 9,180,271 B2 | | 11/2015 | Guo et al. | |
| 9,272,115 B2 | | 3/2016 | Bobey et al. | |
| 9,539,407 B2 | | 1/2017 | Varga et al. | |
| 9,675,775 B2 | | 6/2017 | Bobey et al. | |
| 9,757,528 B2 | | 9/2017 | Rubin | |
| 10,576,221 B2 | | 3/2020 | Faram | |
| 2003/0010344 A1 | * | 1/2003 | Bird | A61M 16/12 128/205.24 |
| 2005/0217666 A1 | | 10/2005 | Fink et al. | |
| 2005/0252509 A1 | * | 11/2005 | Rustad | A61M 16/08 128/203.12 |
| 2006/0120968 A1 | | 6/2006 | Niven et al. | |
| 2006/0283447 A1 | * | 12/2006 | Dhuper | A61M 16/1095 128/203.12 |
| 2007/0101994 A1 | * | 5/2007 | Waters | A61M 16/0833 128/205.12 |
| 2007/0137648 A1 | * | 6/2007 | Addington | A61M 11/06 128/200.14 |
| 2008/0223361 A1 | * | 9/2008 | Nieuwstad | A61M 15/0086 128/200.14 |
| 2008/0264412 A1 | * | 10/2008 | Meyer | A61M 16/0084 128/200.22 |
| 2009/0188500 A1 | | 7/2009 | Faram | |
| 2009/0211571 A1 | * | 8/2009 | Lu | A61M 11/02 128/200.21 |
| 2009/0240192 A1 | * | 9/2009 | Power | B05B 17/0669 604/26 |
| 2009/0260628 A1 | * | 10/2009 | Flynn, Sr. | A61M 16/1065 128/203.29 |
| 2010/0074881 A1 | * | 3/2010 | Boucher | A61P 11/00 514/6.9 |
| 2011/0146670 A1 | | 6/2011 | Gallem et al. | |
| 2012/0103326 A1 | * | 5/2012 | Karle | A61D 7/04 128/200.21 |
| 2013/0081617 A1 | * | 4/2013 | Cavendish | A61M 15/0068 128/203.12 |
| 2014/0373831 A1 | | 12/2014 | Culbertson et al. | |
| 2016/0022933 A1 | * | 1/2016 | Ciancone | A61M 15/0086 128/200.23 |
| 2016/0106947 A1 | | 4/2016 | Flynn | |
| 2016/0114111 A1 | | 4/2016 | Chang | |
| 2017/0007797 A1 | | 1/2017 | Islava | |
| 2018/0085541 A1 | | 3/2018 | Lacy et al. | |
| 2018/0243518 A1 | * | 8/2018 | Sing | A61M 16/0683 |
| 2019/0099577 A1 | | 4/2019 | Fiorenza | |
| 2019/0151572 A1 | * | 5/2019 | Faram | A61M 16/0866 |
| 2020/0054844 A1 | * | 2/2020 | Porée | A61M 15/009 |
| 2020/0129723 A1 | | 4/2020 | Fink et al. | |
| 2021/0187223 A1 | | 6/2021 | Noaeill et al. | |

FOREIGN PATENT DOCUMENTS

| | | | | | |
|---|---|---|---|---|---|
| CN | | 204619102 U | | 9/2015 | |
| CN | | 207024363 U | | 2/2018 | |
| DE | | 9202198 U1 | * | 7/1992 | |
| EP | | 3062853 B1 | | 10/2019 | |
| KR | | 20190091760 A | * | 8/2019 | |
| WO | WO-2005102427 A1 | * | 11/2005 | | A61M 11/02 |
| WO | | 2006102345 A2 | | 9/2006 | |
| WO | | 2007024812 A1 | | 3/2007 | |
| WO | | 2009042187 A1 | | 4/2009 | |
| WO | | 2009117422 A2 | | 9/2009 | |
| WO | | 2014120024 A1 | | 8/2014 | |
| WO | WO-2016116267 A1 | * | 7/2016 | | A61M 15/002 |
| WO | | 2016159889 A1 | | 10/2016 | |

OTHER PUBLICATIONS

Volara System Instructions for Use (196654 REV 3), Product No. PVL1; 2020 by Hill-Rom Services PTE Ltd.; 114 pages.

International Search Report and Written Opinion for International Patent Application No. PCT/SG2022/050206; mailed Jul. 4, 2022; 11 pages.

* cited by examiner

FUNNELED T-CONNECTOR WITH NEBULIZER FOR USE WITH A POSITIVE PRESSURE VENTILATOR

The present application claims the benefit, under 35 U.S.C. § 119(e), of U.S. Provisional Application No. 63/183,239, filed May 3, 2021, which is hereby incorporated by reference herein in its entirety.

BACKGROUND

The present disclosure relates to patient interfaces of respiratory therapy devices and particularly, to a patient interface having a funneled T-connector for use with a nebulizer and a positive pressure ventilator. More particularly, the present disclosure relates to a funneled T-connector that enhances the amount of nebulization of a liquid in a nebulizer cup of the nebulizer.

Nebulizers are typically used to deliver nebulized or aerosolized liquid medication to a patient's airway. Respiratory therapy devices having patient interfaces to which nebulizer cups of nebulizers removably attach are also known. One such respiratory therapy device is the VOL-ARA™ Airway Clearance System which is manufactured by Hill-Rom Services PTE. LTD. of Singapore, Singapore. Sometimes the patient interface that is connected to a nebulizer is also connected to a positive pressure line of a ventilator, such as a positive pressure ventilator or a mechanical ventilator. It is desirable for efficient nebulization to occur so that as much nebulized liquid enters the patient's airway and lungs as possible during nebulization therapy. Thus, there is an ongoing need to improve patient interfaces for delivery of nebulized or aerosolized substances to patients.

SUMMARY

An apparatus, system, or method may comprise one or more of the features recited in the appended claims and/or the following features which, alone or in any combination, may comprise patentable subject matter:

According to the present disclosure, an apparatus for applying positive pressure nebulized liquid to a patient may be provided. The apparatus may include a funneled T-connector that may have a funnel with a first opening of a first diameter, a second opening of a second diameter that may be smaller than the first diameter, and a funnel wall that may extending between the first opening and the second opening. The funnel wall may define a main funnel axis that may extend through centers of the first and second openings. The funneled T-connector further may have a cylindrical nebulizer port that may extend outwardly from the funnel wall along a port axis that may be substantially perpendicular to the main funnel axis. The nebulizer port may define a nebulizer passage that may be in communication with an internal funnel space that may be bounded by the funnel wall. The apparatus also may include a nebulizer cup assembly that may include a nebulizer cup to contain liquid and a nebulizer cap that may be configured to removably attach to a top region of the nebulizer cup. The nebulizer cap may have a cylindrical nebulizer outlet that may be sized and configured to removably attach to the cylindrical nebulizer port. The cylindrical nebulizer outlet may extend upwardly through the nebulizer passage, beyond the cylindrical nebulizer port, and into the internal funnel space such that a top edge of the cylindrical nebulizer outlet may be located in its entirety within the internal funnel space between the funnel wall and the main funnel axis.

In some embodiments, the first opening of the funneled T-connector may define a first circle of the first diameter, the second opening may define a second circle of the second diameter, and the first circle may be substantially parallel with the second circle. Thus, the main funnel axis of the funnel may be a straight axis. Optionally, the cylindrical nebulizer port may terminate at one end at the funnel wall. Further optionally, the nebulizer cap may have a top shoulder surface from which the cylindrical nebulizer outlet may extend and a bottom edge of the cylindrical nebulizer port may abut the top shoulder surface.

The present disclosure contemplates that an airway interface may be coupled to the first opening of the funneled T-connector. For example, the airway interface may include at least one of the following: a mask, a mouthpiece, an endotracheal tube, or a tracheostomy tube. If desired, the apparatus further may include an air delivery unit that may include a first air source to provide pressurized air to the funneled T-connector and a second air source to provide pressurized air to the nebulizer cup assembly. For example, the first air source may include a blower and the second air source may include a pump or a compressor.

In some embodiments, the air delivery unit may include a main housing in which the first air source may be situated and an auxiliary housing in which the second air source may be situated. Optionally, the auxiliary housing may be attachable to and detachable from the main housing. If desired, the auxiliary housing may include a tray that may attach to and detach from a bottom of the main housing. The apparatus further may include a hose through which pressurized air may be provided to the funneled T-connector and a tube though which pressurized air may be provided to the nebulizer cup assembly. The nebulizer cup may include a tube port to which a terminal end of the tube couples.

The present disclosure further contemplates that the apparatus also may include a handle that may have a first end that may be coupled to the funneled T-connector at the second opening and a second end that may be coupled to a terminal end of the hose. The handle may have an internal passage that may be in communication with the internal funnel space of the funneled T-connector. Optionally, the handle may be curved between the first end and the second end. In some embodiments, the cylindrical nebulizer outlet may be configured to couple to the cylindrical nebulizer port with a press fit.

If desired, the apparatus further may include a non-funneled T-connector that may be coupled to the funneled T-connector at the first opening. The non-funneled T-connector may have a main tube that may be substantially perpendicular to the main funnel axis and an auxiliary tube that may intersect the main tube and that may extend therefrom in perpendicular relative therewith. The auxiliary tube may be attached to the funneled T-connector at the first opening, for example. Optionally, the main tube of the non-funneled T-connector may be oriented substantially perpendicularly to the cylindrical nebulizer outlet.

In some embodiments, the apparatus further may include a positive pressure ventilator that may be coupled to a first end of the main tube of the non-funneled T-connector and a second end of the main tube of the non-funneled T-connector may be configured to couple to an airway interface that may be configured for coupling to an airway of a patient. In such embodiments, the apparatus also may include an air delivery unit that may include a first air source to provide pressurized air to the funneled T-connector and a second air source to provide pressurized air to the nebulizer cup assembly. For example, the first air source may include a blower and the second air source may include a pump or a compressor. Alternatively or additionally, the air delivery unit may include a main housing in which the first air source may be situated and an auxiliary housing in which the second air source may be situated. If desired, the auxiliary housing may be attachable to and detachable from the main housing. Optionally, the auxiliary housing may include a tray that may attach to and detach from a bottom of the main housing.

In other embodiments, the apparatus further may include a mechanical ventilator that may have a positive pressure port and a negative pressure port. In such embodiments, the apparatus also may include a Y-connector that may have a first branch for coupling to an airway of a patient, a second branch coupled pneumatically to the positive pressure port of the mechanical ventilator, and a third branch coupled pneumatically to the negative pressure port of the mechanical ventilator. The funneled T-connector may be pneumatically coupled to the second branch of the Y-connector, if desired.

Optionally, the apparatus further may include an inhalation hose that may be pneumatically coupled to the positive pressure port of the mechanical ventilator and to the second branch of the Y-connector for delivery of positive pressure to the patient's airway. Further optionally, the apparatus may include an exhalation hose that may be pneumatically coupled to the negative pressure port of the mechanical ventilator and to the third branch of the Y-connector for application of negative pressure to the patient's airway. If desired, the apparatus further may include an air delivery unit that may have a first air source to provide pressurized air to the funneled T-connector and a second air source to provide pressurized air to the nebulizer cup assembly. For example, the first air source may include a blower and the second air source may include a pump or a compressor. Alternatively or additionally, the air delivery unit may include a main housing in which the first air source may be situated and an auxiliary housing in which the second air source may be situated. Further alternatively or additionally, the auxiliary housing may be attachable to and detachable from the main housing. Optionally, the auxiliary housing may include a tray that may attach to and detaches from a bottom of the main housing.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
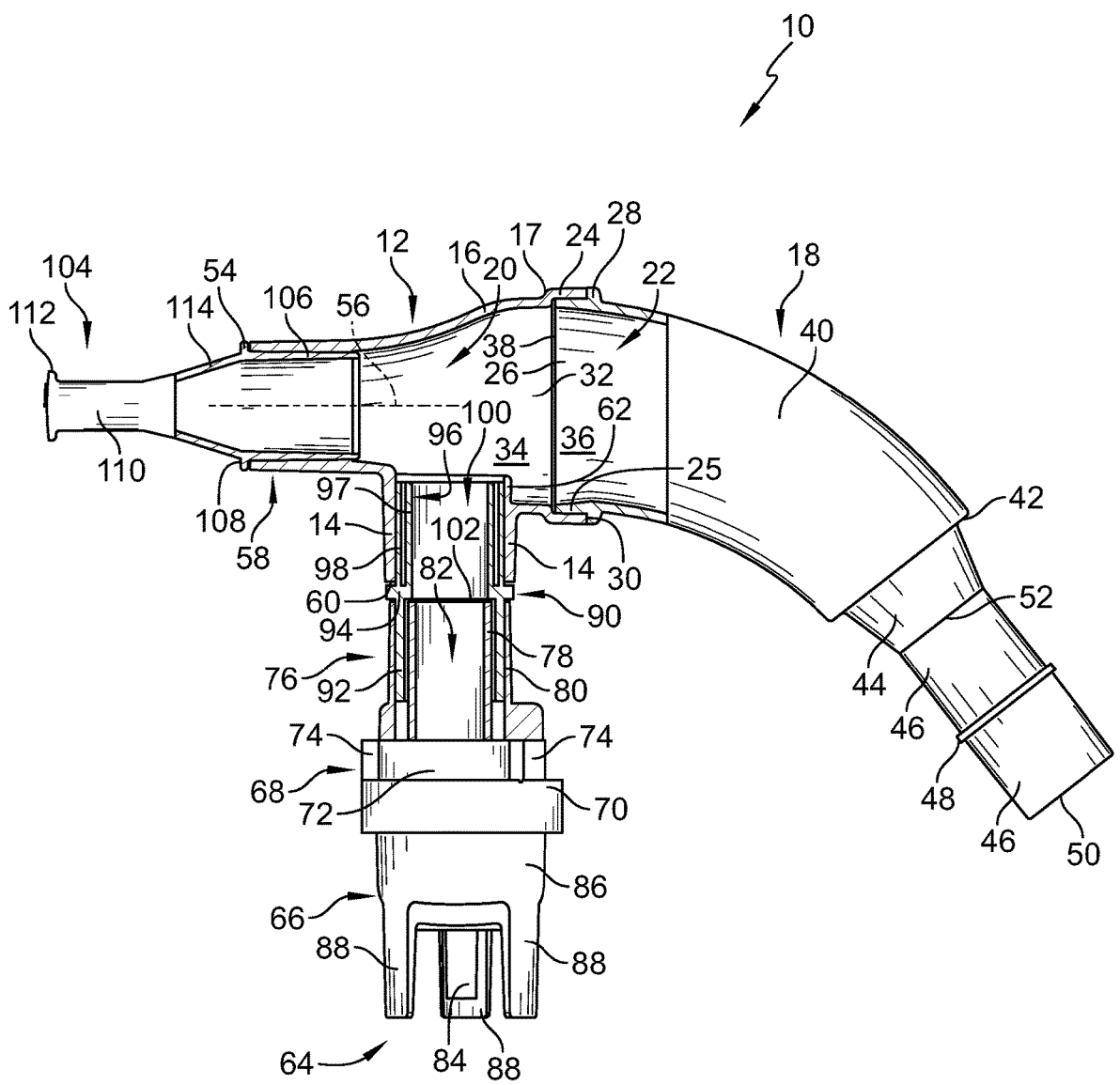
FIG. 1 is a part cross sectional, part side elevation view of a prior art patient interface for a respiratory therapy apparatus showing the prior art interface having a funneled T-connector with cylindrical wall extending downwardly from a funnel wall, an adapter having an upper cylindrical region inserted into the cylindrical wall of the funneled T-connector, and a nebulizer having a nebulizer cap with an upstanding, cylindrical nebulizer outlet attached to a lower cylindrical region of the adapter such that a top edge of the nebulizer outlet is situated beneath a bottom edge of the cylindrical wall of the funneled T-connector.

As shown in FIG. 1, a prior art patient interface 10 of a respiratory therapy apparatus has a funneled T-connector 12 with a cylindrical wall 14 extending downwardly from a funnel wall 16 of the funneled T-connector 12. Patient interface 10 further includes a curved handset 18 that removably couples to funneled T-connector 12 such that an interior region 20 of funneled T-connector 12 is in pneumatic communication with an interior region 22 of the curved handset 18. Funneled T-connector 12 has an annular connection ring 24 that is offset radially outwardly from funnel wall 16 so that a terminal end portion or region 26 of handset 18 is able to be received within a bore defined by the annular connection ring 24. An annular rib 28 is provided around the circumference of end region 26 of handset 18 and a circular end edge 30 of annular connection ring 24 confronts and/or abuts annular rib 28 when funneled T-connector 12 is connected to handset 18 as shown in FIG. 1.

An end region 32 of funneled T-connector 12 and end region 26 of handset 18 are sized similarly so that when T-connector 12 and handset 18 are coupled together, an inner surface 34 of funnel wall 16 and an inner surface 36 of an outer wall 25 of handset 18 are substantially contiguous at an interior seam 38 formed between funneled T-connector 12 and handset 18. The term "substantially" as used in the preceding sentence and elsewhere herein is intended to mean at least within manufacturing tolerances (e.g., +/−0.1% up to +/−10% of a given dimension). Thus, substantially contiguous surfaces 34, 36 form an uninterrupted cylindrical surface that spans across seam 38 between end portions 26, 32. In some embodiments, surface 36 has a nominal diameter of 40.4 millimeters (mm) adjacent to seam 38 and surface 34 has a nominal diameter of 40.6 mm adjacent to seam 38.

Handset 18 has a main portion 40 with a curved, slightly frustoconical shape that extends from an outlet end of handset 18 at seam 38 to an annular shoulder 42. In the illustrative example, planes defined by the outlet end of handset 18 at seam 38 and by shoulder 42 intersect at an included angle of about 52°. Thus, main portion 40 curves through an arc of about 52° in the illustrative example. The word "about" in the preceding sentence and as used elsewhere herein is intended to mean at least within manufacturing tolerances (e.g., +/−0.1% up to +/−10% of a given dimension). Handset 18 further includes a straight frustoconical portion 44 that extends from shoulder 42 away from main portion 40 and that has a diameter which decreases in size as a distance from shoulder 42 increases. Frustoconical portion 44 terminates at a cylindrical inlet portion 46 of handset 18.

Handset 18 includes an annular rib 48 extending radially outwardly from cylindrical inlet portion 46 about midway between a terminal inlet end 50 of handset 18 and a junction 52 between cylindrical inlet portion 46 and frustoconical portion 44 of handset 18. In some embodiments, annular rib 48 is located about 21.0 mm from terminal inlet end 50. Each of portions 40, 42, 44, 46 have a wall thickness of about 2 mm (minimum of 1.9 mm in some embodiments). For example, at the outlet end of handset 18 adjacent to seam 38, an outside diameter of portion 40 is about 44.0 mm. An inlet opening with an inside diameter of about 18.2 mm is provided at terminal inlet end 50 in some embodiments. Between terminal inlet end 50 and annular rib 48, cylindrical inlet portion 46 is shaped so as to meet ISO Standard 5356-1 for 22 mm external taper in some embodiments. Handset 18 is made from any plastics material having suitable durability and strength but, in some embodiments, is made from Acrylonitrile Butadiene Styrene (ABS) PA757 material such as that available from Chi Mei Corporation of Rende, Tainan, Taiwan and having the brand name POLYLAC®.

Still referring to FIG. 1, funneled T-connector 12 includes a terminal outlet end defined by a circular end edge 54 that encompasses an outlet opening having an inside diameter of about 22.37 mm. Between the terminal outlet end defined by end edge 54 and for a distance of about 21 mm, the outlet region of T-connector 12 tapers down to an inner diameter of about 21.85 mm in the illustrative example. Thus, a generally cylindrical outlet region 58 of funneled T-connector 12 is slightly tapered and shaped so as to meet ISO Standard 5356-1 for 22 mm internal taper in some embodiments.

An overall length of funneled T-connector between planes defined by end edge 30 of annular connection ring 24 and end edge 54 of funnel wall 16 is about 69.0 mm in some embodiments. A central axis 56 of funneled T-connector 12 passes through centers of the circular openings defined at outlet end edge 54, seam 38, and end edge 30. From annular connection ring 24 moving toward end edge 54, funnel wall 16 tapers inwardly in a curved manner toward central axis 56 and then blends smoothly in a curved manner into the generally cylindrical outlet region 58 of funnel wall 16 adjacent to end edge 54. Funnel wall 16, therefore, defines inner and outer surfaces of revolution about central axis 56, with the exception of the portion of funnel wall 16 that is intersected by cylindrical wall 14. The overall shape of funnel wall 16, in cross section, resembles a shallow S-curve with a slightly convex outer surface that begins near a stepped transition portion 17 of T-connector 12 and moving toward outlet end edge 54, then transitioning to a slightly concave outer surface about midway between portion 17 and the generally cylindrical outlet region 58 having the tapered inner surface extending from end edge 54 toward inlet edge 30 by about 21 mm as discussed above.

Similar to handset 18, the wall thickness of funnel wall 16 and annular connection ring 24 is about 2 mm (minimum of 1.9 mm in some embodiments), as is the wall thickness of the stepped transition portion 17 that extends radially between wall 16 and ring 24 in the vicinity of seam 38. However, cylindrical outlet region 58 of funnel wall 16 and cylindrical wall 14 that extends downwardly from funnel wall 16 are each shaped so as to meet ISO Standard 5356-1 for 22 mm internal taper in some embodiments, as noted above. In the illustrative example, a perpendicular distance between central axis 56 and a plane defined by a circular bottom edge 60 of cylindrical wall 14 is about 35.9 mm and circular bottom edge 60 encompasses an adapter receiving opening having an inside diameter of about 22.37 mm. Thus, the opening in cylindrical wall 14 at edge 60 is the same size as the opening in funnel wall 16 at end edge 54. An outside diameter of cylindrical wall 14 is about 26.5 mm in some embodiments. A rear portion 62 of cylindrical wall 14 projects upwardly from funnel wall 16 into the interior region 20 of funneled T-connector 12 in the illustrative example. Funneled T-connector 12 is made from any plastics material having suitable durability and strength but, in some embodiments, is made from Polypropylene (PP) P4G4Z-011 material such as that available from Flint Hills Resources, LP of Wichita, Kansas, U.S.A.

With continued reference to FIG. 1, a nebulizer assembly 64, also referred to herein as nebulizer cup assembly 64, includes a nebulizer cup 66 and a nebulizer cap 68 that is removably coupleable to a top region of cup 66 such as with a threaded connection or a snap fit, for example. Cap 68 includes a bottom portion 70, an intermediate portion 72 with grip tabs 74 integrally molded with bottom portion 70, and a dual wall outlet port 76 extending upwardly from intermediate portion 72. Dual wall outlet port 76 includes concentric inner and outer cylindrical walls 78, 80. Inner cylindrical wall 78 provides an outlet passage of the nebulizer assembly 64 and has a bore 82 therethough that communicates pneumatically with an interior region of cup 66. Thus, intermediate portion 72 and bottom portion 70 of cap 68 have spaces that pneumatically communicate with bore 82 and the interior region of cup 66. Cup 66 and cap 68 are separable so that cup 66 can be filled, partially or fully, with liquid medication through the open top of cup 66. Once liquid medication is placed in cup 66, cap 68 is reattached to cup 66.

Nebulizer cup 66 includes a tube port 84 extending downwardly from a central region of a main cup wall 86. Tube port 84 includes a passage therethrough so that pressurized air provided to tube port 84 via a tube having one end coupled to tube port 84 and an opposite end coupled to a pressure source, as will be described in further detail below, enters the interior region of cup 66 to nebulize or atomize or aerosolize (these terms are used interchangeably herein) the liquid medication for upward delivery through bore 82 of inner cylindrical wall 78 of outlet port 76. Nebulizer cup 66 also includes a set of three support legs 88 extending downwardly from main cup wall 86. Legs 88 extend downwardly beyond a bottom of tube port 84. Thus, legs 88 are configured to support cup 66 on an underlying surface such as a table top, for example, while cup 66 is being filled with liquid medication. In the illustrative example, nebulizer assembly 64 is a SIDESTREAM™ nebulizer available from Koninlijke Philips N.V. of Amsterdam, Netherlands.

In the prior art arrangement of FIG. 1, an adapter 90 is used to interconnect funneled T-connector 12 and nebulizer assembly 64. Adapter 90 includes a cylindrical bottom wall 92 configured for insertion into the annular space defined between inner and outer cylindrical walls 78, 80 of outlet port 76 of nebulizer assembly 64. Adapter 90 further includes an annular rib 94 at the top of bottom wall 92 and a dual wall top portion 96 extending upwardly from annular rib 94. Dual wall top portion 96 includes concentric inner and outer cylindrical walls 97, 98. Adapter 90 has a bore 100 therethough that communicates pneumatically with bore 82 of outlet port 76 of nebulizer assembly 64 and with interior region 20 of funneled T-connector 12. Outer cylindrical wall 98 press fits into the bore of cylindrical wall 14 of funneled T-connector 12. Annular rib 94 of adapter is sandwiched between bottom edge 60 of cylindrical wall 14 and a top edge 102 of outlet port 76 of nebulizer assembly 64. Thus, top edge 102 of outlet port 76 of nebulizer cup assembly 64 is situated below bottom edge 60 of cylindrical wall 14 in the prior art arrangement of FIG. 1.

In the illustrative FIG. 1 example, a standard, off-the-shelf mouthpiece 104 is attached to end region 58 of funnel wall 16 of funneled T-connector 12. Mouthpiece 104 includes a cylindrical wall 106 that press fits into end region 58 of funnel wall 16 through the opening defined by end edge 54. An annular rib 108 of mouthpiece 104 engages end edge 54 to limit the insertion of mouthpiece into interior region 20 of funnel wall 16. Mouthpiece 104 further includes a somewhat oval, somewhat rectangular end wall 110 with a flared lip 112 at its distal end and a tapered transition wall 114 that tapers from annular rib 108 to end wall 110. See FIG. 7 for an additional understanding of the shape and geometry of end wall 110 and tapered transition wall 114 of mouthpiece 104.

Figure 2:
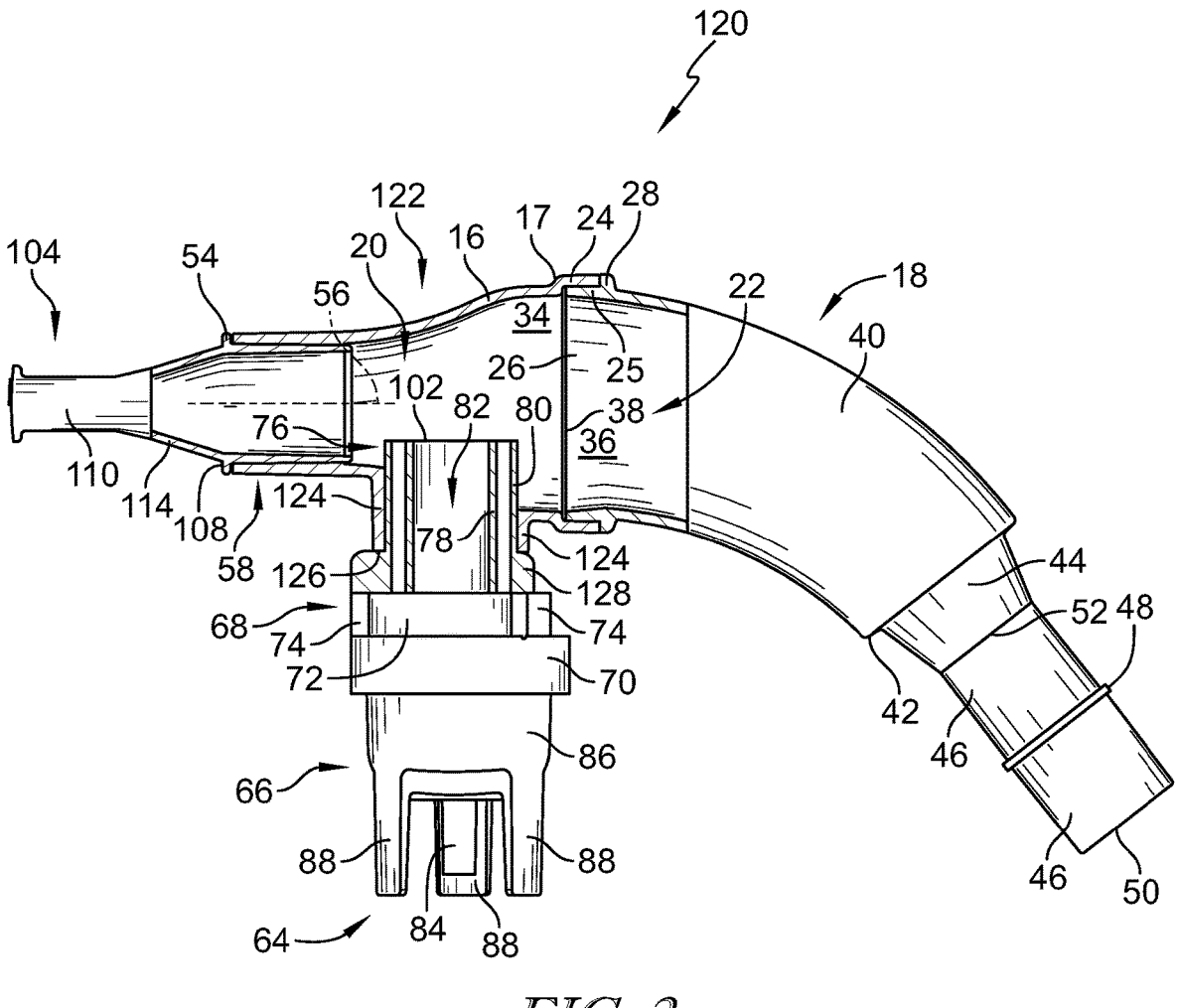
FIG. 2 is a part cross sectional, part side elevation view, similar to FIG. 1, of a modified funneled T-connector in which the adapter of FIG. 1 is omitted and the upstanding, cylindrical nebulizer outlet of the nebulizer cap is inserted through an enlarged-diameter cylindrical wall of the modified funneled T-connector so that the top edge of the nebulizer outlet is situated inside an interior region of the modified funneled T-connector that is defined by the funnel wall of the modified funneled T-connector.

Referring now to FIG. 2, a modified patient interface 120 is shown. Patient interface 120 is similar to patient interface 10 of FIG. 1 and so, where appropriate, the same reference numbers are used to denote portions of patient interface 120 that are the same, or substantially the same, as like portions of patient interface 10. Where like reference numbers are used in connection with portions of patient interface 120, therefore, the descriptions above of the corresponding portions of patient interface 10 are equally applicable to patient interface 120 and the descriptions are not repeated. In other words, in the description that follows, the focus will be on those portions of patient interface 120 that differ from patient interface 10.

Patient interface 120 has a modified funneled T-connector 122 that, for the most part is the same as funneled T-connector 12 of FIG. 1, but that has a cylindrical wall 124 with a geometry that is different than that of cylindrical wall 14 of T-connector 12. In particular, cylindrical wall 124 is shorter and has a larger inside and outside diameter than cylindrical wall 14, although the wall thickness of cylindrical wall 14 is still about 2 mm (minimum of 1.9 mm in some embodiments). More particularly, a perpendicular distance between central axis 56 and a plane defined by a circular bottom edge 126 of cylindrical wall 124 is about 28.0 mm, the inside diameter of cylindrical wall 124 is about 24.88 mm at bottom edge 126, and the outside diameter of cylindrical wall 124 is about 29.0 mm at bottom edge 126. In some embodiments, cylindrical wall 124 has an inner surface that tapers by a similar degree as cylindrical wall 14, but because cylindrical wall 124 is shorter than cylindrical wall 14, the amount of taper is less overall than that of cylindrical wall 14. Also, cylindrical wall 124 does not include any portion, like portion 62 of cylindrical wall 14, that extends from funnel wall 16 into the interior region 20 of funneled T-connector 122 in the illustrative example.

As a result of the cylindrical wall 124 being shorter and having a larger inside diameter than cylindrical wall 14, when nebulizer assembly 64 is attached to Funneled T-connector 122, dual wall outlet port 76 extends upwardly through the bore of cylindrical wall 124 and into the interior region 20 of funnel wall 16 of funneled T-connector 122. More particularly, outer concentric wall 80 press fits into the bore of cylindrical wall 124 and top edge 102 of outlet port 76 is situated inside the interior region 20 of funnel wall 16 of T-connector 122. Thus, bore 82 of interior wall 78 provides an outlet passage directly into the interior region 20 of funnel wall 16 of T-connector 122. Furthermore, circular bottom edge 126 of cylindrical wall 124 engages an annular shoulder portion 128 of dual outlet port 76 to limit the insertion of outlet port 76 into the bore of cylindrical wall 124.

Figure 3:
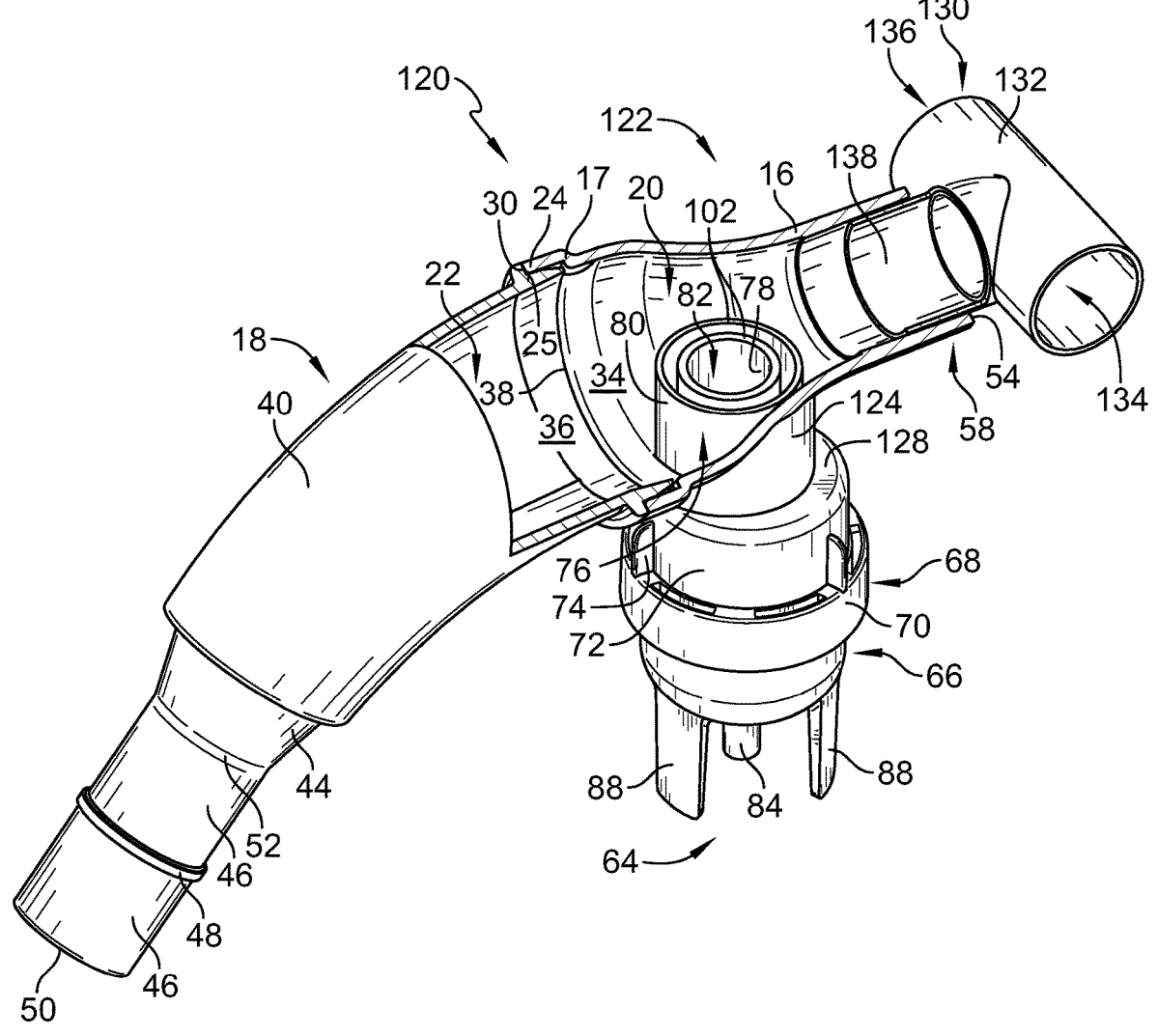
FIG. 3 is a perspective view of the modified funneled T-connector of FIG. 2, with portions broken away, showing the nebulizer outlet received in the interior region defined by the funnel wall and showing a non-funneled T-connector attached to an outlet opening of the modified funneled T-connector.

Referring now to FIG. 3, a perspective view of the modified patient interface 120 having the modified funneled T-connector 122 of FIG. 2 with portions broken away is shown. FIG. 3 further shows the top edge 102 of outlet port 76 actually comprising respective top edges 102 of the concentric walls 78, 80. Thus, in the illustrative embodiment, top edges 102 of walls 78, 80 are substantially coplanar. In other embodiments, one or the other of walls 78, 80 extends further into the interior region 20 of funneled T-connector than the other. In still other embodiments, outlet port 76 of nebulizer cup assembly 64 includes only wall 80 and wall 78 is omitted. In such embodiments, bore 82 of outlet port 76 has a larger diameter than in the depicted embodiment of FIG. 3.

Still referring to FIG. 3, a non-funneled T-connector 130 is press fit into outlet end region 58 of funneled T-connector 122 in lieu of the mouthpiece 104 shown in FIGS. 1 and 2. Non-funneled T-connector includes a main tube 132 that is cylindrical and that has first and second open ends 134, 136. An auxiliary tube 138 intersects main tube 132 about midway between open ends 134, 136 thereby to create the T-shape of non-funneled T-connector 130. It is the auxiliary tube 138 that is press fit into end region 58 of funneled T-connector 122. Regardless of whether mouthpiece 104 or non-funneled T-connector 130 is attached to patient interface 120, in use, a first air stream provided by a first air source (discussed in further detail below) travels from inlet end 50 of handset 18 to outlet end 54 of funneled T-connector 122 and a second air stream provided by a second air source (discussed in further detail below) travels through nebulizer cup assembly 64 to inject nebulized liquid upwardly into the first air stream and then out of patient interface 120 at the outlet end 54. The first air stream produces a Venturi effect to assist in moving the nebulized liquid contained in the second air stream upwardly out of bore 82 of outlet port 76 and into interior region 20 of funneled T-connector 122.

Figure 4:
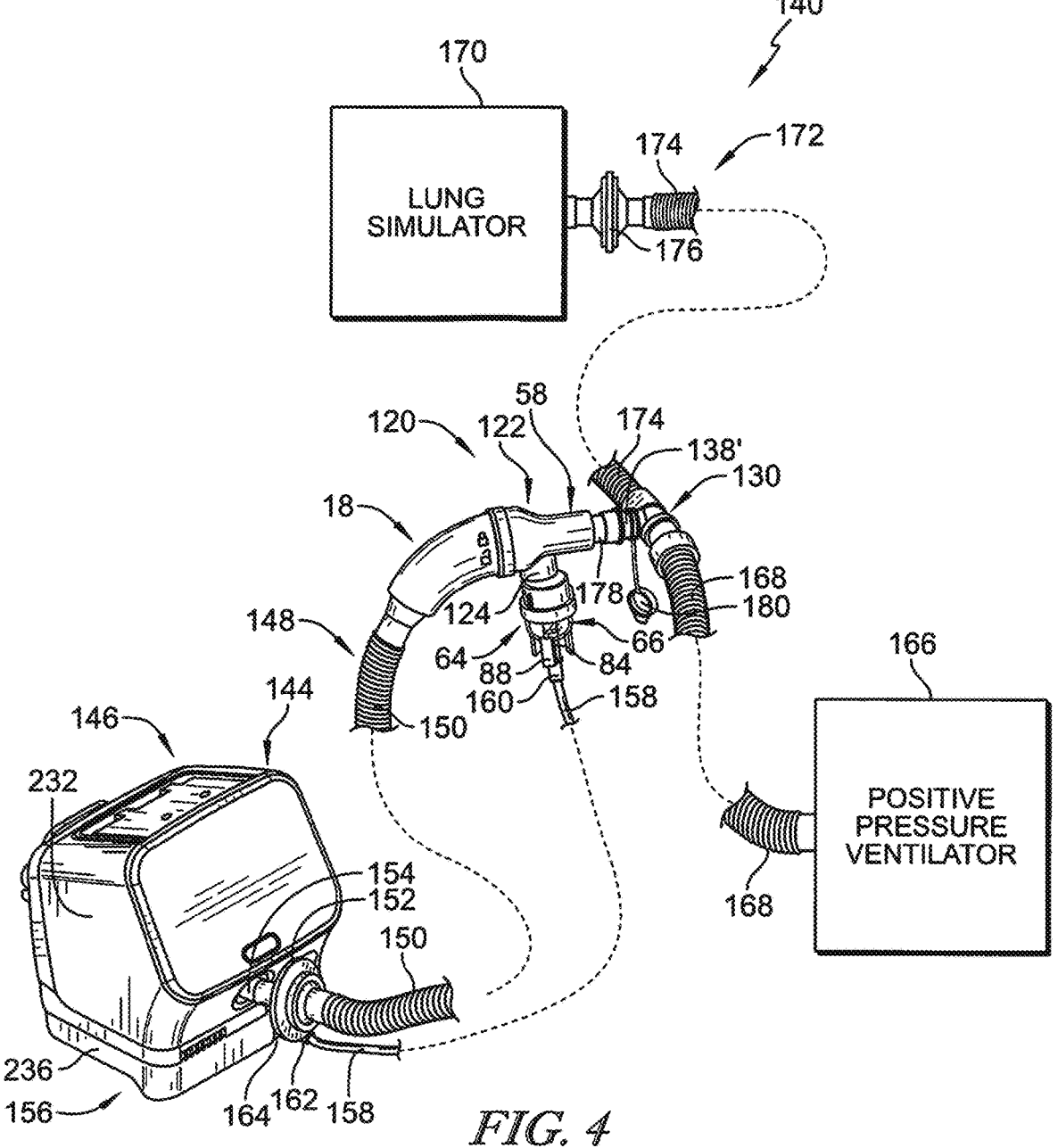
FIG. 4 is a part isometric, part diagrammatic view of a test system in which the modified funneled T-connector of FIG. 3 has an inlet of a curved handle portion coupled to a pressure generator of a respiratory therapy apparatus by a first hose, a nebulizer inlet of a nebulizer cup of the nebulizer coupled to the pressure generator by flexible tube, an inlet of a main tube of the non-funneled T-connector coupled to a positive pressure ventilator by a second hose, and an outlet of the main tube of the non-funneled T-connector coupled to a lung simulator by a third hose.

Referring now to FIG. 4, a part isometric, part diagrammatic view of a test system 140. Test system 140 was used to conduct comparison testing to assess the performance of the prior art patient interface 10 of FIG. 1 with the modified patient interface of FIGS. 2 and 3. In particular, test system 140 was used to evaluate how much liquid in nebulizer cup assembly 64 became nebulized during a test period. In FIG. 4, patient interface 120 is shown in test system 140 but it should be appreciated that patient interface 10 was connected in system 140 in the same manner during its testing.

Figure 8:
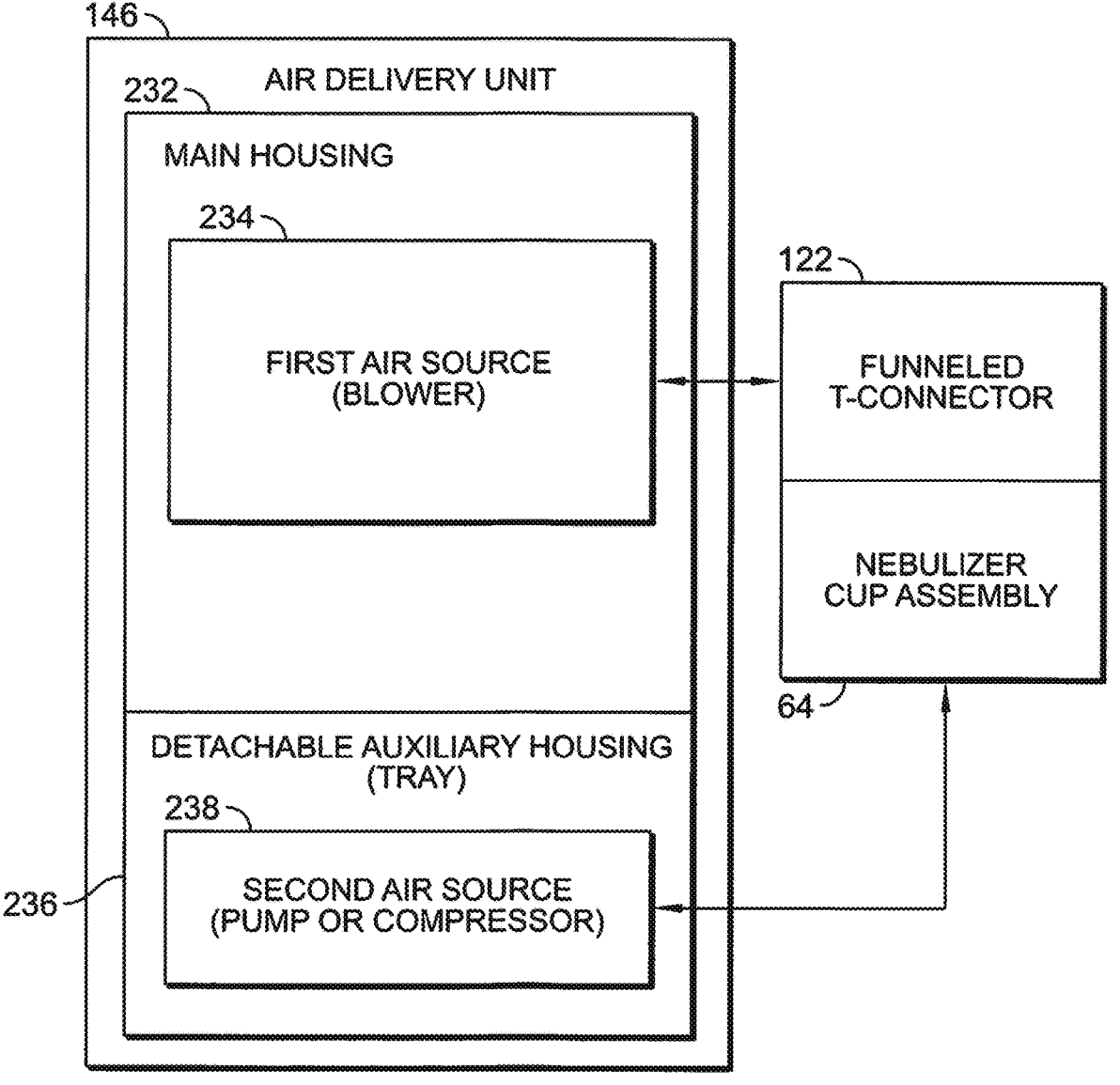
FIG. 8 is a diagrammatic view of the respiratory therapy apparatus of FIG. 2 showing the apparatus including an air delivery unit having first and second air sources.

In test system 140, the inlet end of curved handset 18 is coupled to a first pressure generator portion 144 of a respiratory therapy apparatus 146 (aka an air delivery unit 146) by a first conduit 148. First conduit 148 includes a relatively long (e.g., about 3 to about 5 feet) hose 150 and a filter unit 152 that connects an end of hose 150 to an outlet port 154 of first pressure generator portion 144 of apparatus 146. Pressure generator portion 144 includes a blower 234 that acts the first pressure source mentioned above. Blower 234 is situated in a main housing 232 of air delivery unit 146 as shown diagrammatically in FIG. 8. Also in test system 140 of FIG. 4, tube port 84 of nebulizer cup 66 is coupled to a second pressure generator portion 156 of respiratory therapy apparatus 146 by a flexible tube 158. In particular, flexible tube 158 has a first end connector 160 that attaches to tube port 84 and a second end connector 162 that attaches to an outlet port 164 of second pressure generator portion 156 of apparatus 146. Tube 158 is at least as long as first conduit 148 and in some embodiments, is longer (e.g., about 1 foot to about 3 feet longer) to accommodate movement of nebulizer cup assembly 64 away from patient interface 120 for placement on a table or counter or similar such surface for refilling. Pressure generator portion 156 includes a detachable auxiliary housing 236 (FIG. 8), illustratively embodied as a tray, that is attachable to and detachable from main housing 232. Pressure generator portion 156 further includes a pump or compressor 238 that acts as the second pressure source mentioned above. Second air source 238 is situated in detachable auxiliary housing 236 as shown diagrammatically in FIG. 8. As further shown diagrammatically in FIG. 8, first air source 234 is pneumatically coupled to funneled T-connector 122 and second air source 238 is pneumatically coupled to nebulizer cup assembly 64.

In the illustrative example, respiratory therapy apparatus 146 is the VOLARA™ Airway Clearance System which is manufactured by Hill-Rom Services PTE. LTD. of Singapore, Singapore. Additional details of respiratory therapy apparatus 146 may be found in U.S. application Ser. No. 16/952,166, filed Nov. 19, 2020, now U.S. Pat. No. 11,633, 559, and titled MULTI-MODE RESPIRATORY THERAPY APPARATUS, SYSTEM, AND METHOD which is hereby incorporated by reference herein in its entirety, but see particularly, FIGS. 2-17C and the related discussion which pertains to the external and internal components of apparatus 146, filter unit 152, and prior art patient interface 10. Additional details of a rotary valve assembly used in apparatus 146 may be found in U.S. Pat. No. 10,905,836 which is hereby incorporated by reference herein in its entirety, but see particularly, FIG. 72 and the related discussion.

In test system 140, the first open end 134 of main tube 132 of non-funneled T-connector 130 serves as an inlet of non-funneled T-connector 130 which is coupled to a positive pressure ventilator 166 by a second hose 168. Positive pressure ventilator 166 is illustrated diagrammatically in FIG. 4 but in the embodiment of test system 140 used to evaluate patient interfaces 10, 120, positive pressure ventilator 166 was a PHILIPS® RESPIRONICS® TRILOGY® 200 HC ventilator available from Koninlijke Philips N. V. of Amsterdam, Netherlands. The second open end 136 of main tube 132 of non-funneled T-connector 130 serves as an outlet of non-funneled T-connector 130 which is coupled to a lung simulator by a second conduit 172 which includes a third hose 174 and a filter unit 176. Filter unit 176 is similar to filter unit 152. Lung simulator 170 is illustrated diagrammatically in FIG. 4 but in the embodiment of test system 140 used to evaluate patient interfaces 10, 120, lung simulator 170 was a Series 1101, Model No. 113227-1101 breathing simulator available from Hans Rudolph, Inc. of Shawnee, Kansas, U.S.A.

Still referring to test system 140 of FIG. 4, outlet end region 58 of funneled T-connector 122 of patient interface 120 is coupled to an auxiliary tube 138' of non-funneled T-connector 130 by an adapter 178. Illustratively, adapter 178 is a 22 mm×15 mm adapter. Thus, auxiliary tube 138' in the embodiment of T-connector 130 in FIG. 4 is smaller than the embodiment of T-connector 130 shown in FIG. 3. As also shown in FIG. 4, an end cap 180 is tethered to auxiliary tube 138' and is used to close the open end of tube 138' when no patient interface, such as patient interfaces 10, 120, is being used with the positive pressure ventilator 166.

During the testing of patient interfaces 10, 120 in the test system 140, the respiratory therapy apparatus 146 was operated to deliver a pressure at 20 centimeters of water (cmH$_2$O) in continuous high frequency oscillation (CHFO) mode for ten minutes. Also during testing, positive pressure ventilator 166 was operated at 50 cmH$_2$O in inspiratory positive airway pressure (IPAP), 20 cmH$_2$O expiratory positive airway pressure (EPAP), and 20 breaths per minute (bpm). Further during testing, lung simulator was set to mimic a patient having 50 centimeters/liter (c/L) of lung resistance, 20 milliliters (ml)/cmH$_2$O of lung compliance, 15 cmH$_2$O of amplitude, and 20 bpm. Additionally, nebulizer cup 66 was filled with 3 ml of 0.9% saline solution and was weighted prior to running the test. After ten minutes of operation, the remaining saline solution was weighed to determine the residual volume.

Multiple tests were run for each of patient interfaces 10, 120 in test system 140. For patient interface 10, the residual saline solution in nebulizer cup 66 were as follows: test 1=1.81 ml; test 2=1.78 ml; and test 3=1.80 ml, for an average of 1.80 ml. For patient interface 120, the residual saline solution in nebulizer cup 66 were as follows: test 1=0.97 ml; test 2=0.91 ml; and test 3=0.90 ml, for an average of 0.93 ml. Thus, use of patient interface 120 in test system 140 resulted in 2.07 ml of the original 3 ml of saline solution being nebulized, on average, whereas use of patient interface 10 in test system 140 resulted in only 1.2 ml of the original 3 ml of saline solution being nebulized, on average. This means that use of patient interface 120 as compared to patient interface 10 results in 1.725 times the amount of nebulization (i.e., 2.07 ml/1.2 ml=1.725). Stated another way, there was about a 72.5% increase in the amount of nebulization (i.e., (2.07-1.2)/1.2×100=72.5%) using patient interface 120 as compared to patient interface 10. This substantial increase in the amount of nebulization was an unexpected result of the design changes made to develop patient interface 120. It is believed the unexpected increase in performance may be due to the decrease in the surface area available for the aerosolized solution to condense and/or the shorter runway distance from the nebulizer cup 66 to the main therapy pathway and/or an increase in the Venturi effect due to the enlarged opening of cylindrical wall 124 so that bore 82 is directly accessible in interior region 20 of funneled T-connector 122 (e.g., due to the removal of adapter 90).

Figure 5:
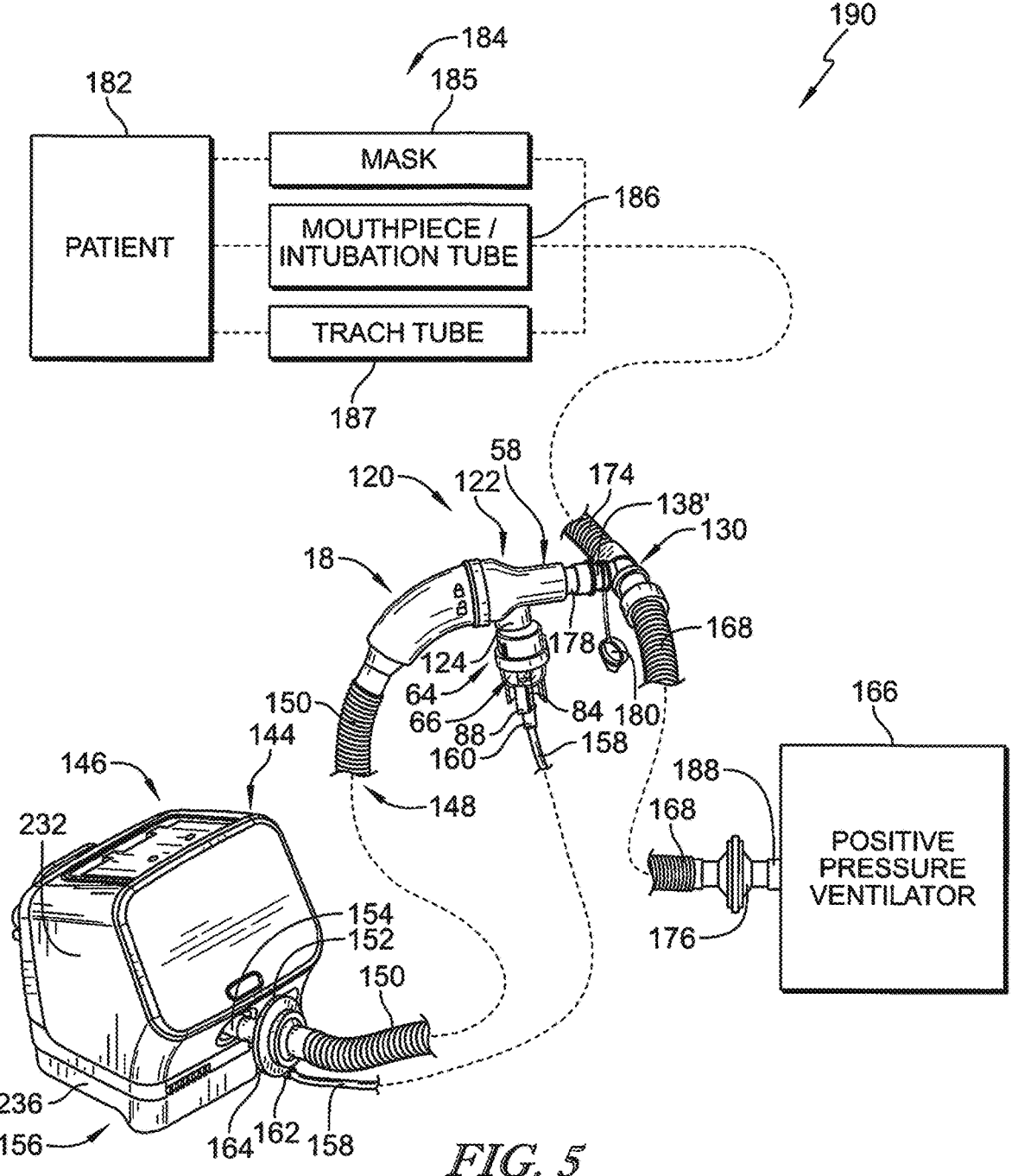
FIG. 5 is a part isometric, part diagrammatic view, similar to FIG. 4, but omitting the lung simulator and showing the third hose alternatively being coupleable to one of a set of alternative patient interfaces including a mask, a mouthpiece or intubation tube (aka an endotracheal tube), or to a tracheostomy tube (aka a trach tube) which are, in turn, coupleable to a patient.

Referring now to FIG. 5, a part isometric, part diagrammatic view is provided of a system 190 that is similar to test system 140 of FIG. 4 but that omits lung simulator 170 and having third hose 174 alternatively being coupleable to an airway of a patient 182 via one of a set of alternative patient interfaces 184. The examples of patient interfaces 184 shown in FIG. 5 include a mask 185, an intraoral appliance 186 such as a mouthpiece or intubation tube (aka an endotracheal tube), and a tracheostomy tube (aka a trach tube) 187. Whether to use mask 185, appliance 186, or trach tube 187 in system 190 is at the discretion of the medical professionals treating the patient 182. If a mouthpiece is used as the appliance 186, it may be mouthpiece 104 of FIGS. 1 and 2 but attached to the end of hose 174, possibly with the use of an adapter, rather than being attached to patient interface 120.

In system 190, filter unit 176 is coupled to an outlet port 188 of positive pressure ventilator 166. Thus, filter unit 176 is interposed between an end of second hose 168 and outlet port 188. Otherwise, all of the elements of system 190 are the same as the elements of system 140 and so the same reference numbers are used in FIG. 5 as were used in FIG. 4 for like components. The descriptions of these like components set forth above in connection with system 140 of FIG. 4 are equally applicable to system 190 of FIG. 5. Of course, the various operational settings of respiratory therapy apparatus 146 and positive pressure ventilator 166 is at the discretion of the medical professionals treating the patient 182 and so ventilation of the patient 182 by system 190 may occur at settings other than those mentioned above in connection with test system 140. Furthermore, the liquid placed in nebulizer cup 66 may be any liquid that is nebulized and used to treat a patient and therefore, may be different than the saline solution used in test system 140, again, at the discretion of the medical professionals treating the patient 182.

Figure 6:
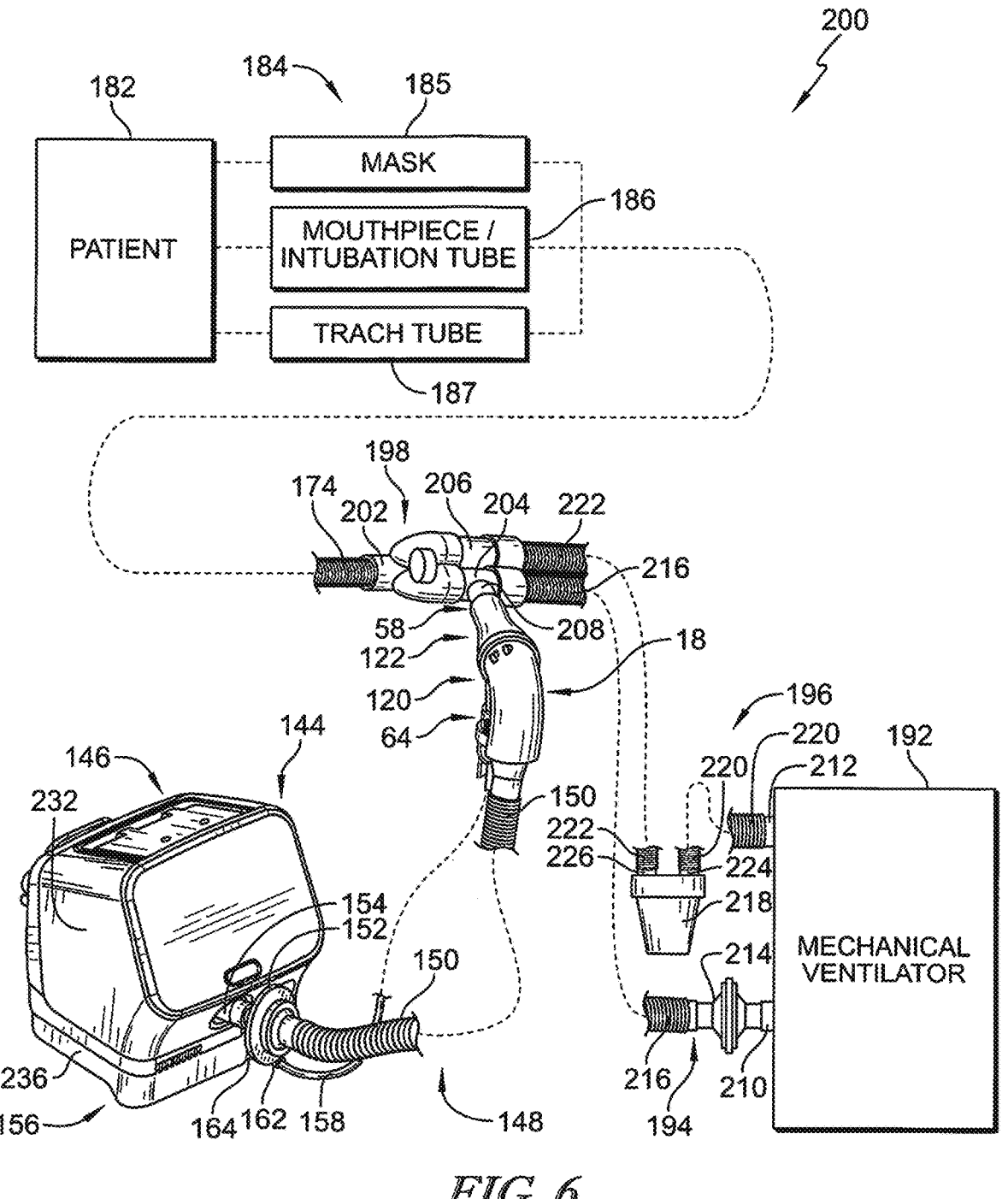
FIG. 6 is a part isometric, part diagrammatic view, similar to FIG. 5, but omitting the positive pressure ventilator and replacing it with a mechanical ventilator having separate positive pressure and negative pressure ventilation lines, and omitting the non-funneled T-connector and replacing it with a Y-connector having a first branch coupled to an airway of a patient via a selected one of the alternative patient interfaces, a second branch coupled pneumatically to a positive pressure port of the mechanical ventilator via the positive pressure line, and a third branch coupled pneumatically to a negative pressure port of the mechanical ventilator via the negative pressure line which includes a sputum collection canister and a pair of hose segments, the outlet of the funneled T-connector being pneumatically coupled to the second branch of the Y-connector.

Referring now to FIG. 6, a part isometric, part diagrammatic view is provided of a system 200 that is similar to system 190 of FIG. 5 but that omits positive pressure ventilator 166 and replaces it with a mechanical ventilator 192 having separate positive pressure and negative pressure ventilation lines or conduits 194, 196. Another difference between system 190 and system 200 is that system 200 omits the non-funneled T-connector 130 and replaces it with a Y-connector 198 having a first branch 202, a second branch 204, and a third branch 206. Branches 202, 204, 206 have pneumatic passages therethrough such that branches 204, 206 are each pneumatically in communication with branch 202. A cylindrical branch 208 tees in to and pneumatically communicates with branch 204. Outlet end region 58 of funneled T-connector 122 of patient interface 120 receives a distal end of cylindrical branch 208 therein so that patient interface 120 is pneumatically coupled to branch 204 of Y-connector 198.

The elements of system 200 that are the same as the like elements of systems 140, 190 discussed above in connection with FIGS. 4 and 5, respectively, are denoted by like reference numbers and the descriptions of these like components set forth above in connection systems 140, 190 of FIGS. 4 and 5, respectively, are equally applicable to system 200 of FIG. 6. Branch 202 of Y-connector 198 is coupled pneumatically to an airway of a patient via hose 174 and a selected one of the alternative patient interfaces 184 such as mask 185, intraoral appliance 186 (e.g., mouthpiece or intubation tube aka endotracheal tube). Second branch 204 of Y-connector 198 is coupled pneumatically to a positive pressure port 210 of mechanical ventilator 192 via positive pressure line 194. Third branch 206 of Y-connector 198 is coupled pneumatically to a negative pressure port 212 of mechanical ventilator 192 via negative pressure line 196.

In the illustrative embodiment, positive pressure line 194 includes a filter unit 214 and a positive pressure hose 216. Filter unit 214 is substantially the same as filter units 152, 176 discussed above and is interposed between positive pressure port 210 and an end of hose 216. Thus, filter unit 214 filters the positive pressure air exiting port 210 of mechanical ventilator 192. Further in the illustrative embodiment, negative pressure line 196 includes a sputum collection canister 218 and a pair of hose segments 220, 222. Hose segment 220 pneumatically interconnects negative pressure port 212 of mechanical ventilator 192 and a first port 224 at the top of canister 218. Hose segment 222 pneumatically interconnects a second port 226 at the top of canister 218 with branch 206 of Y-connector 198.

Mechanical ventilator 192 is a life support ventilator that breathes for the patient 182. Thus, during the patient's inhalation or inspiratory phase, positive pressure is applied to the airway of the patient 182 via positive pressure line 194, branches 202, 204 of Y-connector 198, hose 174, and the selected one of patient interfaces 184, typically an endotracheal tube 186 or tracheostomy tube 187. Nebulized substances, typically nebulized medication, is delivered to the airway of the patient 182 by virtue of the connection of apparatus 146, hose 150, tube 158, and patient interface 120 to branch 204 of Y-connector 198 via cylindrical branch 208. During the patient's exhalation or expiratory phase, negative pressure is applied to the airway of the patient via negative pressure line 196, branches 202, 206 of Y-connector 198, hose 174, and the selected one of patient interfaces 184. Any sputum from the patient 182 that is drawn through this negative pressure exhalation path is deposited in canister 218 so as not be drawn into the internal componentry of mechanical ventilator 192.

In some alternative embodiments of system 200, hose 174 is split into two hose segments and canister 218 is interposed between the hose segments of hose 174 so as to collect the patient's sputum closer to the patient 182. In such alternative embodiments, positive pressure is delivered through the interior region of canister 218 and so is not the ideal arrangement. In other embodiments of system 200, an additional filter unit, similar to filter unit 214, interconnects the selected patient interface 184 and an end of hose 174. In such embodiments, the patient's sputum collects in a lower region of a housing of the filter unit right after it exits from the patient interface 184. However, the volume of space for sputum collection in the housing of the filter unit is not as large as that of canister 218. In still other embodiments of system 200, hose 174 is omitted and branch 202 of Y-connector 198 pneumatically connects to the selected patient interface 184, either directly or via an intervening filter unit. If needed, various adapters are provided at the junctions between the various components of these alternative embodiments of the positive pressure and negative pressure flow paths of system 200.

Figure 7:
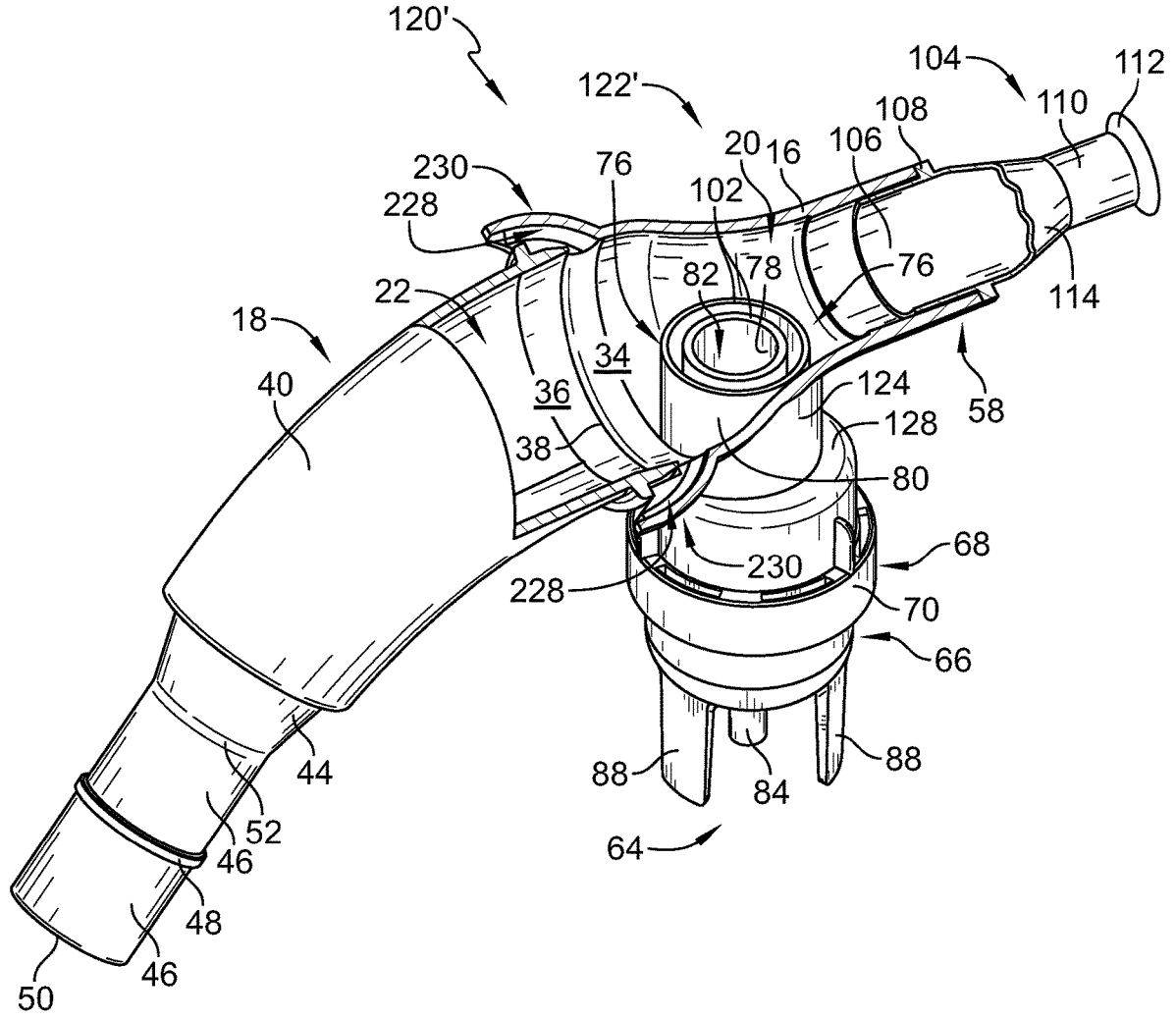
FIG. 7 is a perspective view of the modified funneled T-connector with portions broken away, similar to FIG. 3, showing the nebulizer outlet received in the interior region defined by the funnel wall, showing a pair of ambient air entrainment tabs extending radially outwardly from an inlet region of the funneled T-connector, and showing a mouthpiece attached to the outlet opening of the modified funneled T-connector.

Referring now to FIG. 7, a perspective view with portions broken away of an alternative patient interface 120' having an alternative funneled T-connector 122' is shown. Patient interface 120' of FIG. 7 is similar to patient interface 120 of FIG. 3 and so, where appropriate, the same reference numbers are used to denote portions of patient interface 120' that are the same, or substantially the same, as like portions of patient interface 120. Where like reference numbers are used in connection with portions of patient interface 120', therefore, the descriptions above of the corresponding portions of patient interface 120 are equally applicable to patient interface 120' and the descriptions are not repeated. In other words, in the description that follows, the focus will be on those portions of patient interface 120' that differ from patient interface 120.

Funneled T-connector 122' includes a pair of ambient air entrainment tabs 230 extending radially outwardly from funnel wall 16 at the air inlet region of funneled T-connector 122'. Tabs 230 are spaced apart by about 180 degrees with respect to the circular inlet opening defined by the inlet end region of funnel wall 16. Each entrainment tab 230 includes an air entrainment passage 228 therethrough. In the illustrative example of patient interface 120', mouthpiece 104 is attached to outlet end region 58 of funneled T-connector 122'. This is because funneled T-connector 122' is typically used by a patient that inhales and exhales directly through mouthpiece 104.

Patient interface 120' is shown herein to demonstrate that it is possible to attach nebulizer assembly 64 by press fitting outlet port 76 into and through cylindrical wall 124 while also using funneled T-connector 122' having entrainment tabs 230 with passages 228. When the patient inhales through mouthpiece 104, ambient air enters interior region 20 of funneled T-connector 122' through passages 228 of tabs 230 and mixes with the pressurized air being delivered to inlet end 50 of patient interface 120' by respiratory therapy apparatus 146. The nebulized air being delivered upwardly through bore 82 of cylindrical wall 78 of outlet port 76 also mixes with the pressurized air being delivered to the patient via mouthpiece 104. The downside is that, when the patient exhales, it is possible that some of the nebulized substance contained within interior region 20 of funneled T-connector 122' is blown out to the ambient surroundings through passages 228 of tabs 230. However, provision of funneled T-connector 122' with tabs 230 having passages 228 makes it easier for the patient to exhale through their mouth during the provision of respiratory therapy. Accordingly, patient interface 120' shown in FIG. 7 may be suitable for patients who are, for whatever reason, unable to exhale through their hose or have limited ability to exhale through their nose but that still need respiratory therapy involving delivery of nebulized substances.

Patient interface 120' was attached to test system 140 for analysis in the same manner that patient interface 120 was attached. That is, mouthpiece 104 was omitted from patient interface 120' and non-funneled T-connector attached in its place. A comparable prior art patient interface with entrainment tabs included in funneled T-connector 12 like that of patient interface 10 of FIG. 1 and including cylindrical wall 14 with adapter 90 used to connect nebulizer cup assembly 64 to wall 14 was also tested using test system 140. Such a prior art arrangement is shown and described, for example, in U.S. application Ser. No. 16/952,166, filed Nov. 19, 2020, now U.S. Pat. No. 11,633,559, and titled MULTI-MODE RESPIRATORY THERAPY APPARATUS, SYSTEM, AND METHOD which is already incorporated by reference herein in its entirety, but see particularly, FIG. 9 (elements 444 and 445) and the related discussion.

The residual saline solution in nebulizer cup 66 of the comparable prior art patient interface with entrainment tabs and cylindrical wall 14 used in the test was 1.52 ml, on average, whereas the residual saline solution in nebulizer cup 66 of patient interface 120' with entrainment tabs 230 and cylindrical wall 124 used in the test was 0.99 ml, on average. Thus, while there was slightly more residual saline solution in cup 66 when patient interface 120' was tested as compared to when patient interface 120 was test (i.e., 0.99 ml on average as compared to 0.93 ml on average), the improved performance of patient interface 120' compared to the prior arrangement still represented unexpected results.

It should be noted that there was no exhalation or expiratory phase that was modeled in test system 140 during the testing of patient interface 120' and the comparable prior art arrangement. Having 0.99 ml of residual saline solution means that 2.01 ml out of the original 3 ml of saline solution was nebulized, on average, during the testing of patient interface 120'. Similarly, having 1.52 ml of residual saline solution means that 1.48 ml out of the original 3 ml of saline solution was nebulized, on average, during the testing of the comparable prior art patient interface. In any event, use of patient interface 120' with entrainment tabs 230 and cylindrical wall 124 as compared to the comparable prior art arrangement results in 1.358 times the amount of nebulization (i.e., 2.01 ml/1.48 ml=1.358). Stated another way, there was about a 35.8% increase in the amount of nebulization (i.e., (2.01−1.48)/1.48)×100=35.8%) using patient interface 120' as compared to the comparable prior art patient interface.

Although certain illustrative embodiments have been described in detail above, variations and modifications exist within the scope and spirit of this disclosure as described and as defined in the following claims.

The invention claimed is:

1. An apparatus for applying positive pressure nebulized liquid to a patient, the apparatus comprising a funneled T-connector having a funnel with a first opening of a first diameter, a second opening of a second diameter that is smaller than the first diameter, and a funnel wall extending between the first opening and the second opening, the funnel wall defining a main funnel axis that extends through centers of the first and second openings, the funneled T-connector further having a cylindrical nebulizer port extending outwardly from the funnel wall along a port axis that is substantially perpendicular to the main funnel axis, the nebulizer port defining a nebulizer passage that is in communication with an internal funnel space bounded by the funnel wall, and a nebulizer cup assembly including a nebulizer cup to contain liquid and a nebulizer cap configured to removably attach to a top region of the nebulizer cup, the nebulizer cap having a cylindrical nebulizer outlet that is sized and configured to removably attach to the cylindrical nebulizer port, the cylindrical nebulizer outlet being arranged in substantially perpendicular relation with the main funnel axis and extending upwardly through the nebulizer passage, beyond the cylindrical nebulizer port, and into the internal funnel space such that a top edge of the cylindrical nebulizer outlet is located in its entirety within the internal funnel space between the funnel wall and the main funnel axis, wherein the cylindrical nebulizer outlet comprises a dual wall outlet port that includes concentric inner and outer cylindrical walls that are spaced apart and that both terminate at the top edge such that air passing through the internal funnel space along the main funnel axis moves across exposed ends of the concentric inner and outer cylindrical walls to produce a Venturi effect that draws nebulized liquid into the internal space from a bore defined by the inner cylindrical wall of the dual wall outlet port.

2. The apparatus of claim 1, wherein the first opening defines a first circle of the first diameter, the second opening defines a second circle of the second diameter, and the first circle is substantially parallel with the second circle.

3. The apparatus of claim 2, wherein the main funnel axis does not intersect the cylindrical nebulizer outlet.

4. The apparatus of claim 1, wherein the cylindrical nebulizer port terminates at one end at the funnel wall.

5. The apparatus of claim 1, wherein the nebulizer cap has a top shoulder surface, wherein the cylindrical nebulizer outlet extends from the top shoulder surface, and wherein a bottom edge of the cylindrical nebulizer port abuts the top shoulder surface.

6. The apparatus of claim 1, further comprising an airway interface coupled to the first opening of the funneled T-connector.

7. The apparatus of claim 6, wherein the airway interface comprises at least one of the following: a mask, a mouthpiece, an endotracheal tube, or a tracheostomy tube.

8. The apparatus of claim 1, further comprising an air delivery unit including a first air source to provide pressurized air to the funneled T-connector and a second air source to provide pressurized air to the nebulizer cup assembly.

9. The apparatus of claim 8, wherein the first air source comprises a blower and the second air source comprises a pump or a compressor.

10. The apparatus of claim 8, wherein the air delivery unit comprises a main housing and an auxiliary housing, wherein the first air source is situated in the main housing, and wherein the second air source is situated in the auxiliary housing, the auxiliary housing being attachable to and detachable from the main housing.

11. The apparatus of claim 10, wherein the auxiliary housing comprises a tray that attaches to and detaches from a bottom of the main housing.

12. The apparatus of claim 8, further comprising a hose through which pressurized air is provided to the funneled T-connector and a tube through which pressurized air is provided to the nebulizer cup assembly.

13. The apparatus of claim 12, wherein the nebulizer cup includes a tube port and wherein a terminal end of the tube couples to the tube port.

14. The apparatus of claim 12, further comprising a handle having a first end coupled to the funneled T-connector at the second opening and a second end coupled to a terminal end of the hose, the handle having an internal passage in communication with the internal funnel space of the funneled T-connector.

15. The apparatus of claim 14, wherein the handle is curved between the first end and the second end.

16. The apparatus of claim 1, wherein the cylindrical nebulizer outlet is configured to couple to the cylindrical nebulizer port with a press fit.

17. The apparatus of claim 1, further comprising a non-funneled T-connector coupled to the funneled T-connector at the second opening.

18. The apparatus of claim 17, wherein the non-funneled T-connector has a main tube that is substantially perpendicular to the main funnel axis and an auxiliary tube that intersects the main tube and extends from the main tube in perpendicular relation with the main tube, the auxiliary tube being attached to the funneled T-connector at the first opening.

19. The apparatus of claim 18, wherein the main tube of the non-funneled T-connector being oriented substantially perpendicularly to the cylindrical nebulizer outlet.

20. The apparatus of claim 18, further comprising a positive pressure ventilator coupled to a first end of the main tube of the non-funneled T-connector and a second end of the main tube of the non-funneled T-connector being configured to couple to an airway interface that is configured for coupling to an airway of a patient.

21. The apparatus of claim 20, further comprising an air delivery unit including a first air source to provide pressurized air to the funneled T-connector and a second air source to provide pressurized air to the nebulizer cup assembly.

22. The apparatus of claim 21, wherein the first air source comprises a blower and the second air source comprises a pump or a compressor.

23. The apparatus of claim 21, wherein the air delivery unit comprises a main housing and an auxiliary housing, wherein the first air source is situated in the main housing, and wherein the second air source is situated in the auxiliary housing, the auxiliary housing being attachable to and detachable from the main housing.

24. The apparatus of claim 23, wherein the auxiliary housing comprises a tray that attaches to and detaches from a bottom of the main housing.

25. The apparatus of claim 1, further comprising a mechanical ventilator having a positive pressure port and a negative pressure port and further comprising a Y-connector having a first branch for coupling to an airway of a patient, a second branch coupled pneumatically to the positive pressure port of the mechanical ventilator, and a third branch coupled pneumatically to the negative pressure port of the mechanical ventilator, the funneled T-connector being pneumatically coupled to the second branch of the Y-connector.

26. The apparatus of claim 25, further comprising an inhalation hose pneumatically coupled to the positive pressure port of the mechanical ventilator and to the second branch of the Y-connector for delivery of positive pressure to the patient's airway and further comprising an exhalation hose pneumatically coupled to the negative pressure port of the mechanical ventilator and to the third branch of the Y-connector for application of negative pressure to the patient's airway.

27. The apparatus of claim 25, further comprising an air delivery unit including a first air source to provide pressurized air to the funneled T-connector and a second air source to provide pressurized air to the nebulizer cup assembly.

28. The apparatus of claim 27, wherein the first air source comprises a blower and the second air source comprises a pump or a compressor.

29. The apparatus of claim 27, wherein the air delivery unit comprises a main housing and an auxiliary housing, wherein the first air source is situated in the main housing, and wherein the second air source is situated in the auxiliary housing, the auxiliary housing being attachable to and detachable from the main housing.

30. The apparatus of claim 29, wherein the auxiliary housing comprises a tray that attaches to and detaches from a bottom of the main housing.

* * * * *